United States Patent [19]

Kauffman et al.

[11] Patent Number: 5,041,238
[45] Date of Patent: Aug. 20, 1991

[54] O,O'-BRIDGED OLIGOPHENYLENE LASER DYES, DYESTUFF LASERS AND METHODS OF LASING THEREWITH

[75] Inventors: Joel M. Kauffman, Wayne, Pa.; Charles J. Kelley, West Roxbury, Mass.; Richard N. Steppel, Dayton, Ohio

[73] Assignee: Exciton Chemical Company, Dayton, Ohio

[21] Appl. No.: 236,264

[22] Filed: Aug. 22, 1988

Related U.S. Application Data

[63] Continuation of Ser. No. 830,336, Feb. 18, 1986, abandoned.

[51] Int. Cl.$^5$ ............... C09K 11/06; H01S 3/20
[52] U.S. Cl. ............... 252/301.17; 252/301.21; 252/301.32; 548/440; 585/27; 372/53
[58] Field of Search ............... 252/301.17, 301.21, 252/301.32; 372/53; 585/27; 548/440

[56] References Cited

U.S. PATENT DOCUMENTS

| | | | |
|---|---|---|---|
| 2,414,118 | 1/1947 | Orchin | 585/27 |
| 3,600,445 | 8/1971 | Wirth et al. | 252/301.17 |
| 3,673,219 | 6/1972 | Hay | 252/301.17 |
| 3,736,524 | 5/1973 | Drexhage | 252/301.17 |
| 3,774,122 | 11/1973 | Webster | 372/53 |
| 3,822,270 | 7/1974 | Reynolds | 372/53 |
| 3,873,940 | 3/1975 | Drexhage | 372/53 |
| 3,895,945 | 7/1975 | Watarai et al. | 548/440 |
| 3,904,982 | 9/1975 | Dienes et al. | 252/301.17 |
| 3,939,115 | 2/1976 | Wang et al. | 252/402 |
| 4,005,092 | 1/1977 | Reynolds | 372/53 |
| 4,072,911 | 2/1978 | Hartig et al. | 252/301.17 |
| 4,079,082 | 3/1978 | Hammond et al. | 260/576 |
| 4,100,509 | 7/1978 | Waither et al. | 252/301.17 |
| 4,208,501 | 6/1980 | Yee et al. | 252/301.17 |
| 4,256,900 | 3/1981 | Raue | 252/301.17 |
| 4,274,062 | 6/1981 | Brinkmann et al. | 252/301.17 |
| 4,326,066 | 4/1982 | Eckstein | 252/301.17 |
| 4,338,258 | 7/1982 | Brinkwerth et al. | 558/413 |
| 4,646,309 | 2/1987 | Asisawa et al. | 372/53 |
| 4,876,029 | 10/1989 | Gusten et al. | 252/301.17 |

FOREIGN PATENT DOCUMENTS 1050029  3/1979  Canada.
3408028  9/1985  Fed. Rep. of Germany.
2156374 10/1985  United Kingdom.

OTHER PUBLICATIONS

"Synthesis and Properties of Oxido-P-Oligophenylenes", Macromol. Chem. 86, 139-167 (1965), Wirth et al.

"Photophysical and Laser Properties of New Organic Laser Dyes in the Blue and Ultraviolet Spectral Region", Kernforschungszent, Karlsruhe (1984), Kfk 3810, Sep. 1984, Rinke.

(List continued on next page.)

Primary Examiner—John F. Niebling
Assistant Examiner—Steven P. Marquis
Attorney, Agent, or Firm—Wood, Herron & Evans

[57] ABSTRACT

Disclosed are organic laser dyes and more particularly o,o'-bridged oligophenylene laser dyes which when excited to lase emit radiation in various ranges and especially in the ultraviolet and violet ranges, that is, from about 300 nm to about 420 nm, of the light spectrum. An organic laser dye of this invention comprises an oligophenylene having at least one biphenyl moiety bridged between adjacent ortho positions via a single atom or a plural of atom substituents of various sizes. In one most preferred embodiment, the substituent bonded to the phenyl moieties forming the bridge is a carbon atom free of benzylic hydrogens. The bridging substituent can also be other atoms or groups free of reactive substituents. In another most preferred embodiment, the o,o'-bridged oligophenylene laser dyes are free of vinylene groups bonded directly to the phenyl moieties forming the oligophenylene chains. The o,o'-bridged oligophenylene laser dyes of the present invention are provided with relatively high power output and have relatively long photochemical lifetimes. Also disclosed are dye lasers and methods of lasing.

22 Claims, 3 Drawing Sheets

OTHER PUBLICATIONS

Gusten et al, Chem Abst 104: 198428c (1986).
Wirth et al, Chem Abst 60: 5363a (1963).
Wirth et al., Chem. Abstracts 60 (1963) col. 5363d.
Wirth et al., Chemical Abstracts, vol. 60, col. 5416d.
Wirth et al., Chemical Abstracts, vol. 64, (1966), col. 19529–19532.
Lengyel, "Lasers" Second Edition Wiley–Interscience, New York, pp. 243–245, 252–253.
Chemical Abstracts 104: 198428c, Guesten et al, DE 3408028, 9-12-1985, p. 804.
Chemical Abstracts 102: 122727n, Rinke, p. 611.
Chemical Abstracts, 107: 225508z, Kauffman et al, Laser Chem. 1987 7(5-6), 343–351, p. 523.

O,O'-BRIDGED OLIGOPHENYLENE LASER DYES, DYESTUFF LASERS AND METHODS OF LASING THEREWITH

This application is a continuation, of U.S. application Ser. No. 830,336, filed 2/18/86.

FIELD OF THE INVENTION

This invention relates to organic laser dyes, to dye lasers and methods of lasing that make use of those laser dyes. More particularly, this invention relates to o,o'-bridged oligophenylene dyes which, when excited to lase, emit radiation in various ranges and especially in the ultraviolet and violet ranges, that is, from about 300 nm to about 420 nm, of the light spectrum. In one preferred form, the bridged moiety can be a carbon atom free of benzylic hydrogens or other atoms or groups free of reactive substituents. In another preferred form, there are no vinylene groups bonded directly to the phenyl moieties forming the oligophenylene chains.

BACKGROUND OF THE DISCLOSURE

A laser is a light-amplifying device capable of producing high intensity coherent monochromatic light concentrated in a well-collimated beam, commonly referred to as a laser beam. A typical laser comprises an optical resonator having a laser-active material, i.e., a laser medium, that can be a solid, a liquid or a gas. By operation of the laser, the laser medium's atoms or molecules are excited until they lase, that is, until they emit photons or quanta of light. To excite the atoms or molecules into the lasing state, i.e., pumping, they are subjected to electron or photon bombardment. Upon photon emission, such photons can further trigger other molecules to emit similar photons prematurely and together they form the laser beam. Lasers have a wide variety of uses in such diverse areas as drilling, spectroscopy, welding, cutting, communication, analysis, surgery, and photochemistry.

A laser normally can function only in a small portion of the light spectrum since it is dependent upon the laser medium employed therewith. This is particularly true since the wavelengths emitted by a specific energy transition in a given laser medium is tunable over only a very limited portion of the light spectrum. It is therefore necessary to provide a number of different laser media in order to enable lasers to operate over the entire light spectrum. Many of the laser media available up to now have been solids or gases. However, organic dyes in solution also have been employed and are referred to as "laser dyes". It has been recognized that organic laser dyes in solution can provide advantages not possible with gas or solid laser media. For example, there are several organic laser dyes known that are operable over a relatively broad range of wavelengths. Also, organic laser dyes are capable of being tuned so as to choose a specific wavelength of emission from a range of wavelengths. This is a clear advantage over gaseous or solid laser media which emit at a single wavelength or at very few specific wavelengths. Further, a single laser dye instrument, i.e., a single dye laser, can emit laser beams at widely different wavelengths simply by changing the organic laser dye solution used therewith.

Organic dye lasers and organic laser dyes, however, are not without their shortcomings and disadvantages notwithstanding their known benefits. Some of the problems that are common with known organic laser dyes include poor solubility and steady decline in the power of the laser beam output (whether that beam is continuous or pulsed) as irreversible photodegradation of the organic dyes and/or solvents occurs. Consequently, the useable photochemical "lifetime" or total energy obtained from a given volume of an organic dye in a solvent may be unsatisfactorily short or small.

Notwithstanding the number of known benefits associated with organic laser dyes available today, there is a need to provide new and improved commercially acceptable organic laser dyes that are suitable for lasing. More particularly, there is a need to provide new, improved and more efficient commercially acceptable organic laser dyes that are suitable for lasing especially in the 300-420 nm range as well as other ranges in the light spectrum which are relatively more soluble and relatively more stable photochemically during use so as to provide relatively longer useful lifetimes.

SUMMARY OF THE INVENTION

The present invention is directed to a new and improved class of organic laser dyes, dye lasers and methods of lasing therewith. The new and improved organic laser dyes of this invention are more efficient than their predecessors and can be classified generally as o,o'-bridged oligophenylenes. These o,o'-bridged oligophenylenes overcome certain of the above-mentioned problems heretofore associated with known organic laser dyes that lase in various regions of the light spectrum and in particular that lase in the ultraviolet and violet regions of the light spectrum, and also afford certain advantages. For example, the o,o'-bridged oligophenylenes can emit efficiently laser beams at a variety of wavelengths of the light spectrum and especially in the ultraviolet and violet regions, that is, from about 300 nm to about 420 nm. The o,o'-bridged oligophenylene laser dyes of the present invention also are provided with relatively high power output and have relatively long photochemical lifetimes. And further, some of the o,o'-bridged oligophenylenes are relatively more soluble in laser type solvents that are in practical use today.

In a preferred form, the present invention is directed to novel oligophenylene laser dyes which have at least one biphenyl moiety bridged between adjacent ortho positions. The bridge between adjacent ortho positions may be a single atom substituent or a plural of atom substituents of various sizes. For instance, when the bridge comprises a plural of atom substituents, it may be for example an ethylene bridge in the simplest case.

The novel o,o'-bridged oligophenylene laser dyes are represented by the following general formula:

wherein X represents O, S, SO, $SO_2$, $SiH_2$, SiHR', $SiR'_2$, PH, PR', P(O)R', NH, NR', $CH_2$, CHR' and $CR'_2$ groups; R' represents alkyl, aryl, substituted alkyl and aryl, halogen, alkoxy, alkoxyalkyl, aryloxy, dialkylamino and dialkylaminoalkyl and salts thereof, trialkylaminoalkyl salts, sulfonic, alkylsulfonic, alkylphosphonic and alkylcarboxylic acids, esters and salts thereof, and fluorinated alkyl and aryl groups; R equals H, alkyl, aryl, substituted alkyl and aryl, halogen, alkoxy, alkoxyalkyl, aryloxy, dialkylamino and dialkylaminoalkyl and salts thereof, trialkylaminoalkyl salts, sulfonic, alkylsulfonic, alkylphosphonic and alkylcarboxylic acids, esters and salts thereof, fluorinated alkyl and aryl, NH$_2$, NHR' and NR'$_2$ and salts thereof, PH, PR' and P(O)R'; and n represents 1 to about 4. It will be understood by those of skill in the art that the R groups need not be identical.

In one most preferred form, the present invention is directed to o,o'-bridged oligophenylene laser dyes wherein the bridge is formed with a carbon atom free of benzylic hydrogens. It is believed that the o,o'-bridged oligophenylene laser dyes are relatively more soluble in laser solvents and relatively less reactive when the bridged moiety is a carbon atom free of benzylic hydrogens or other non-reactive substituents.

In another most preferred form, the present invention is directed to o,o'-bridged oligophenylene laser dyes wherein the phenyl moieties forming the oligophenylene chains are free of vinylene groups bonded directly thereto. It is believed that the o,o'-bridged oligophenylene laser dyes have relatively longer photochemical lifetimes when there are no vinylene groups bonded directly to the phenyl moieties of the oligophenylene chains.

The present invention further resides in a dye laser comprising a pumping light source associated with a reservoir, the pumping light source having the ability to excite a dye solution to lase, the dye solution comprising a solvent which does not interfere with lasing and an organic laser dye comprising an oligophenylene having at least one biphenyl moiety bridged between adjacent ortho positions. The solvent may be a polar solvent such as an aqueous solvent which includes alcohol and alcohol-water mixtures. Typical dye laser pumps include gas lasers, excimer lasers, flashlamps, metal vapor lasers and solid state lasers.

Still further, the present invention contemplates a method of emitting laser radiation at various wavelengths which includes the steps of subjecting a laser medium comprising an organic laser dye of this invention to a suitable pumping light source to excite the laser medium to emit radiation.

The above features and advantages of the present invention will be better understood with reference to the accompanying figures, and to the detailed description and examples set out below. It will also be understood that the particular organic laser dyes, dye lasers and methods embodying this invention are exemplary only and not to be regarded as a limitation of the invention.

DESCRIPTION OF THE DRAWINGS

The invention is further described and illustrated in connection with the drawings in which.

DETAILED DESCRIPTION OF THE INVENTION

The present invention is directed to a class of organic laser dyes suitable for lasing in various regions of the light spectrum and especially in the ultraviolet and violet regions, that is, from about 300 nm to about 420 nm, when subjected to a suitable pumping light source. These compounds are referred to as o,o'-bridged oligophenylenes, and they each comprise an oligophenylene having at least one biphenyl moiety, but no more than about four biphenyl moieties, wherein at least one biphenyl moiety is bridged between adjacent ortho positions. It is believed that the bridge between adjacent ortho positions restricts rotation of the phenyl groups, thus resulting in a significant enhancement of the quantum yield of fluorescence and providing a more efficient laser dye. In other words, it is believed that a higher percentage of photon output per photon of excitation is experienced with the laser dyes of this invention relative to oligophenylenes per se.

The bridge may comprise numerous substituents which can vary in size as exemplified herein. For example, in the most simplest case when the bridge is formed of a plurality of substituents, the bridge may be formed of, for instance, an ethylene group generating a six-membered ring between the biphenyl moiety. Nevertheless, it is believed at this time that a single atom bridge forming a five-membered ring in between the biphenyl moiety is most effective. In one most preferred form, however, the bridge should be formed with a carbon atom that is free of benzylic hydrogens. The phrase "biphenyl moiety bridged between adjacent ortho positions" as used herein means a ring ensemble comprised of at least two or more phenyl groups wherein the phenyl groups are directly joined to each other at the 1,1' and/or 4,4' positions and joined or "bridged" to each other via a substituent at either the 2,2' or the 6,6' ortho positions or at both the 2,2' and 6,6' ortho positions. This can be easily illustrated by the following exemplary structure wherein X corresponds to the bridging substituent:

It should be further understood that the term "oligophenylene" as used herein means a compound containing up to about eight phenyl groups wherein the phenyl groups are directly joined to each other at the 1,1' or 4,4' positions or both the 1,1' and 4,4' positions to form a continuous chain. Of course, the organic laser dyes of this invention may contain more than about eight phenyl groups since there may be additional phenyl groups attached to the substituents or radicals attached to the oligophenylene as already indicated herein.

The new organic laser dyes of the present invention can be represented by the following general formula:

As indicated, substituent X may be a single atom or a plurality of atoms. For instance, substituent X may comprise O, S, SO, SO$_2$, SiH$_2$, SiHR', SiR'$_2$, PH, PR', P(O)R', NH, NR', CH$_2$, CHR' and CR'$_2$ groups.

Possible substituents for R' are alkyl, aryl, substituted alkyl and aryl, halogen, alkoxy, alkoxyalkyl, aryloxy, dialkylamino and dialkylaminoalkyl and salts thereof, trialkylaminoalkyl salts, sulfonic, alkylsulfonic, alkylphosphonic and alkylcarboxylic acids, esters and salts thereof, and fluorinated alkyl and aryl. Preferably, however, substituent X is oxygen, CR'$_2$ or NR' to form a stable five-membered ring between the adjacent phenyl groups.

Possible substituents for each R are H, alkyl, aryl, substituted alkyl and aryl, halogen, alkoxy, alkoxyalkyl, aryloxy, dialkylamino and dialkylaminoalkyl and salts thereof, trialkylaminoalkyl salts, sulfonic, alkylsulfonic, alkylphosphonic and alkylcarboxylic acids, esters and salts thereof, fluorinated alkyl and aryl, NH$_2$, NHR' and NR'$_2$ and salts thereof, PH, PR' and P(O)R'. It should be understood as previously stated that each R substituent does not have to be the same, and that the R substituent may be substituted on one or more positions of the same ring or at same or different positions on different rings.

As previously indicated, n is 1 to about 4. The preferred organic laser dyes of the formula illustrated are those in which n is 2. The organic laser dyes which are believed at this time to be preferred are 3,3'-bi(dibenzofuran), 9,9,9',9'-tetrapropyl2,2'-bifluorene, 3-phenyldibenzofuran, 9,9'-dipropylfluorene, 2,2'-bifluorene, and 9,9'-diethyl-2,2'-bicarbazole.

It is further discovered that when substituent X of the bridged biphenyl moiety is a carbon atom which is free of benzylic hydrogens, the laser dye is relatively less reactive and relatively more soluble. In other words, it has been realized that the absence of benzylic hydrogens from the bridged carbon substituent, that is, the carbon substituent that is bonded directly to the phenyl moieties to form the bridge, renders the organic laser dyes of the present invention less reactive and more soluble. In view of the present disadvantages concerning the solubility of organic laser dyes available hitherto, this is quite significant. For example, 9,9,9',9'-tetrapropylbifluorene is more soluble than 2,2'-bifluorene in solvents. It has been found that 9,9,9',9'-tetrapropyl-2,2'-bifluorene has a solubility of 9.3×10$^{-3}$M or 4.6 g/l in DMF whereas 2,2'-bifluorene has a solubility of 1.0×10$^{-3}$M or 0.33 g/l in DMF as indicated in Table I. Further, since benzylic hydrogens are believed to be reactive to free radicals and to bases rendering such laser dyes unstable, it is believed at this time that some of the most preferred laser dyes of this invention are those laser dyes that have a carbon atom free of benzylic hydrogens as the bridged substituent or other bridging groups free of reactive substituents.

Also disclosed are organic laser dyes suitable for lasing when subjected to a pumping light source comprising an oligophenylene having at least one biphenyl moiety bridged between adjacent ortho positions wherein each phenyl group forming the continuous oligophenylene chain is free of vinylene groups bonded directly thereto. It is believed that when the phenyl groups forming the oligophenylene chain are free of vinylene groups bonded directly thereto, the organic laser dyes have relatively longer photochemical lifetimes. Therefore, in another most preferred form, the organic laser dyes of this invention comprise an oligophenylene having at least one biphenyl moiety bridged between adjacent ortho positions wherein there are no vinylene groups bonded directly to the oligophenylene phenyl groups. By vinylene groups, it is meant herein a substituent having the vinyl grouping —CH=CH—.

Examples of potential laser solvents which might be used with this invention and which might not hinder stimulated emission are: water; monohydric and polyhydric alcohols, for example, methanol, ethanol, isopropanol, butanol, ethylene glycol and glycol monoethylether; cyclic ethers, such as tetrahydrofuran and dioxane; aromatic compounds, such as benzene, toluene, phenol, resorcinol and cresols; ketones, such as acetone, 2-butanone and cyclohexanone; esters, such as ethyl acetate, diethyl malonate, glycol diacetate and diethyl carbonate; perfluorinated hydrocarbons; and fluorinated alcohols, for example, hexafluoroisopropanol; and other solvents, such as cyclohexane, decalin, chloroform, dimethylsulfoxide, dimethylformamide, dimethylacetamide.

Also, as indicated herein, one of the unique and remarkable features of this invention is that the solubilities of the novel organic laser dyes, in solvents commonly used for laser dyes, are significantly greater than those of unsubstituted quaterphenyls as demonstrated in Table I. The improved solubilities make the dyes of the present invention potentially more useful for lasing.

TABLE I

| | SOLUBILITIES OF o,o'-BRIDGED OLIGOPHENYLENES AT 21° C. | | | | |
|---|---|---|---|---|---|
| Solvent | 3-phenyldibenzofuran | 2,2'-bifluorene | 9,9'-dipropylfluorene | 3,3'-bi(dibenzofuran) | 9,9,9',9'-tetrapropyl-2,2'-bifluorene |
| cyclohexane | greater than 1.0 × 10$^{-2}$M or 2.44 g/l | 3.0 × 10$^{-5}$M or 0.01 g/l | — | 9.0 × 10$^{-5}$M or 0.030 g/l | 2.0 × 10$^{-2}$M or 10 g/l |
| 1,2-dichloroethane | —. | 1.0 × 10$^{-3}$M or 0.33 g/l | — | — | — |
| DMF* | — | 1.0 × 10$^{-3}$M or 0.33 g/l | — | 2.5 × 10$^{-3}$M or 0.84 g/l | 9.3 × 10$^{-3}$M or 4.6 g/l |
| dioxane | — | — | — | 1.3 × 10$^{-3}$M or 0.43 g/l | 6.5 × 10$^{-3}$M or 3.2 g/l |
| 100% ethanol | 1.6 × 10$^{-2}$M or 3.9 g/l | 2.3 × 10$^{-5}$M or 0.0077 g/l | — | 6.3 × 10$^{-5}$M or 0.021 g/l | 7.8 × 10$^{-4}$M or 0.39 g/l |
| 95% ethanol | 1.1 × 10$^{-2}$M or 2.7 g/l | 1.1.3 × 10$^{-3}$M or 0.4 g/l | — | 1.0 × 10$^{-2}$M or 2.5 g/l | — |
| 50% ethanol | 8.4 × 10$^{-3}$M or | — | — | — | — |

TABLE I-continued

SOLUBILITIES OF o,o'-BRIDGED OLIGOPHENYLENES AT 21° C.

| Solvent | 3-phenyldi-benzofuran | 2,2'-bifluorene | 9,9'-dipropyl-fluorene | 3,3'-bi(di-benzofuran) | 9,9,9',9'-tetrapropyl-2,2'-bifluorene |
|---|---|---|---|---|---|
| Methanol | 2.0 g/l $1.2 \times 10^{-2}$M or 2.9 g/l | — | — | $2.1 \times 10^{-5}$M or 0.007 g/l | $3.4 \times 10^{-4}$M or 0.17 g/l |
| Toluene* | — | $1.3 \times 10^{-3}$M or 0.4 g/l | — | $2.4 \times 10^{-3}$M or 0.8 g/l | — |

*For comparison, BBQ, 4,4'''-bis(2-butyloctyloxy)quaterphenyl, which is a well known laser dye, dissolve in DMF to the extent of $1.0 \times 10^{-3}$M and the solubility for quaterphenyl in toluene is only about $1.3 \times 10^{-3}$M or 0.4 g/l. In addition, 3-phenyldibenzofuran is much more soluble in methanol, 50% ethanol, 95% ethanol and absolute ethanol than p-terphenyl, a commonly employed laser dye.

As another unique feature, the organic laser dyes of the present invention are provided with relatively high power output and have relatively long photochemical lifetimes especially in the 300–420 nm range. For example, 2,2'-bifluorene has an unexpectedly, relatively high power output, as shown in Table II, when pumped at 308 nm by a xenon-chloride excimer laser in a dioxane/methanol solvent. As can be realized from Table II, 2,2'-bifluorene, in comparison to known lasing dyes, has a much higher output energy at equal concentrations than p-terphenyl, butyl-PBD and BBQ.

TABLE II

RELATIVE OUTPUT AND LASING WAVELENGTH MAXIMUM IN NANOMETERS OF LASER DYES IN THE ULTRAVIOLATE RANGE

| Organic Laser Dye | Lasing Wavelength Maximum | Output Energy | Solvent |
|---|---|---|---|
| p-terphenyl | 335 nm | 2.6 units | dioxane |
| Butyl-PBD | 370 nm | 1.9 units | ethanol/toluene |
| 2,2'-bifluorene | 375 nm | 3.1 units | dioxane/methanol |
| BBQ | 385 nm | 2.4 units | dioxane |

In addition, 2,2'-bifluorene surprisingly lased flashlamp pumped at 358 nm in ethanol and at 395 nm in dimethylformamide. The 2,2'-bifluorene that was used was produced in accordance with the procedures disclosed in L.-S. Wen and P. Kovacic, *Tetrahedron*, 34:2723(1978) which is incorporated herein in its entirety by reference. The compound 2,2'-bifluorene can be represented by the following structure:

2,2'-Bifluorene

With respect to 9,9,9'9'-tetrapropyl-2,2'bifluorene and 3,3'-bi(dibenzofuran), they both have unexpectedly, relatively high power output energies, as shown in Table III, when pumped at 308 nm by a xenon chloride excimer laser in a dioxane solvent. As can be realized from Table III, 9,9,9'9'-tetrapropyl2,2'-bifluorene and 3,3'-bi(dibenzofuran) have much higher output energies, that is, they are about 27% and 70% greater, respectively, than the known laser dye BBQ. Also, it can be observed from Table III that 9,9,9'9'-tetrapropyl-2,2'-bifluorene and 3,3'-bi(dibenzofuran) lased, xenon-chloride excimer laser pumped, at about 383 nm and 375 nm, respectively, in dioxane. The compounds 9,9,9'9'-tetrapropyl-2,2'-bifluorene and 3,3'-bi(dibenzofuran) can be represented by the following structures:

9,9,9',9'-Tetrapropyl-2,2'-bifluorene 3,3'-Bi(dibenzofuran)

TABLE III

RELATIVE OUTPUT AND LASING WAVELENGTH MAXIMUM IN NANOMETERS OF LASER DYES IN THE ULTRAVIOLET RANGE

| Organic Laser Dye | Lasing Wavelength Maximum | Relative Output Energy | Solvent |
|---|---|---|---|
| 9,9,9',9'-tetrapropyl-2,2'-bifluorene | 383 nm | 7.6 units | dioxane |
| 3,3'-bi(dibenzofuran) | 375 nm | 10.2 units | dioxane |
| BBQ | 386 nm | 6.0 units | dioxane |

The dyes of this invention can be stimulated, i.e., optically pumped, with the aid of energy sources by means of, for example, electrons or light. Examples of light sources include gas lasers, such as nitrogen, argon-ion and krypton-ion lasers, and excimer lasers, such as xenon chloride and krypton fluoride lasers. Still further, the dyes of this invention may be pumped with flashlamps, metal vapor lasers and solid state lasers.

Figure 6:
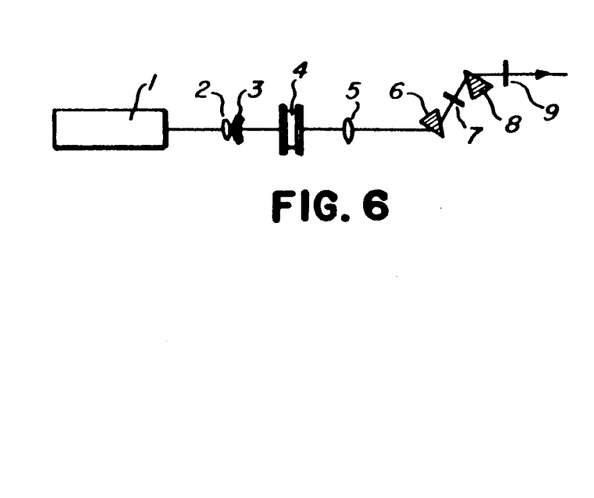
FIG. 6 is a schematic illustration of an exemplary dye laser suitable for use with this invention.

With reference to FIG. 6, the exemplary dye laser illustrated therein consists of a gas laser 1, a focus lens 2, a laser resonator, and external prism 8 and a filter 9. The laser resonator consists of a spherical mirror 3 with a dichroic reflective coating which reflects the dye laser light from 4 but passes the excitation from laser 1 and a plain mirror 7. The dye solution, which circulates through the dye cell 4 at a selected flow speed, is excited with gas laser 1. For this purpose, a pumping light is focused into cell 4 by means of lens 2. The lens 5 serves to match the mode volume of the resonator to the optically pumped dye volume.

A rough wavelength selection is made by means of dispersion of a prism 6 which is placed in the beam at the Brewster angle. The laser is tuned by rotating this prism. A second external prism 8 serves to turn the laser beam into the horizontal. While particular reference is made to a laser as exemplified in FIG. 6, other types of laser systems not inconsistent with the teachings of this invention may also be employed. The dye laser depicted in FIG. 6 has been disclosed and described for illustrative purposes only.

A few organic laser dyes in accordance with the present invention will now be further illustrated by reference to the following examples.

EXAMPLE 1

9,9-Dipropylfluorene

The dye, 9,9-dipropylfluorene, was prepared as follows. A solution of 57.5 g of 9,9-diallyfluorene in 110 ml of ethyl acetate was hydrogenated over 0.6 g of 5% palladium on carbon at 3 atm. in a Paar apparatus for 4.5 hrs. The catalyst was removed by filtration, and the solvent was removed under reduced pressure. The resulting oil was crystallized from methanol with chilling to give 34.7 g of product, mp 42°–44° C. Recrystallization from methanol gave 28.4 g (45% of theory) of the product, mp 44°–6° C. Further crystallization from methanol or acetonitrile gave the analytical sample, mp 49°–50° C. NMR (CDCl$_3$): δ0.67 (s, 10H, —CH$_2$CH$_3$), 1.91 (m, 4H, —CH$_2$—), 7.21 (m, 6H, aromatic), 7.6 (m, 2H, H-4 and H-5).

Anal. Calcd. for C$_{19}$H$_{22}$: C, 91.14; H, 8.86%. Found: C, 90.88; H, 8.63%.

Figure 1:
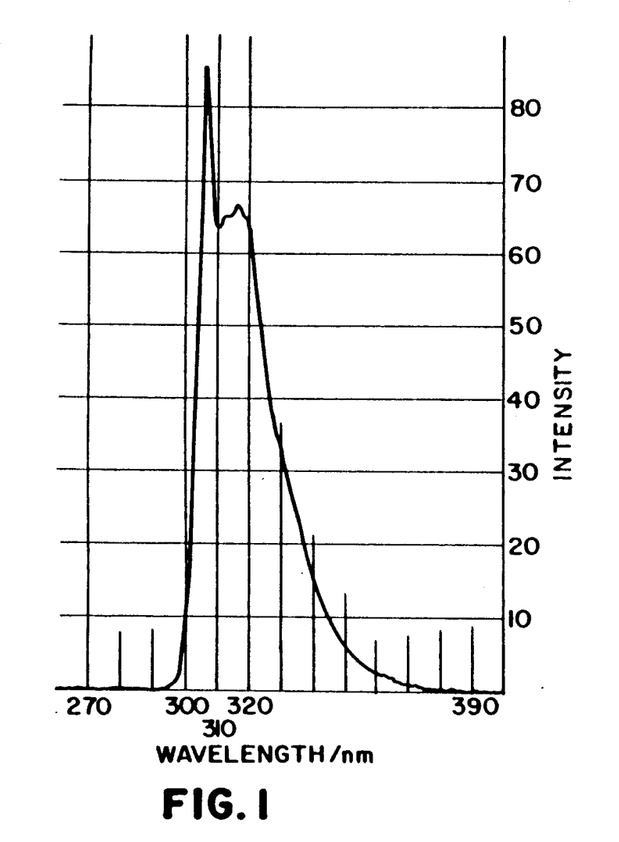
FIG. 1 is a fluorescence emission spectrum of 9,9-dipropylfluorene.
Figure 5:
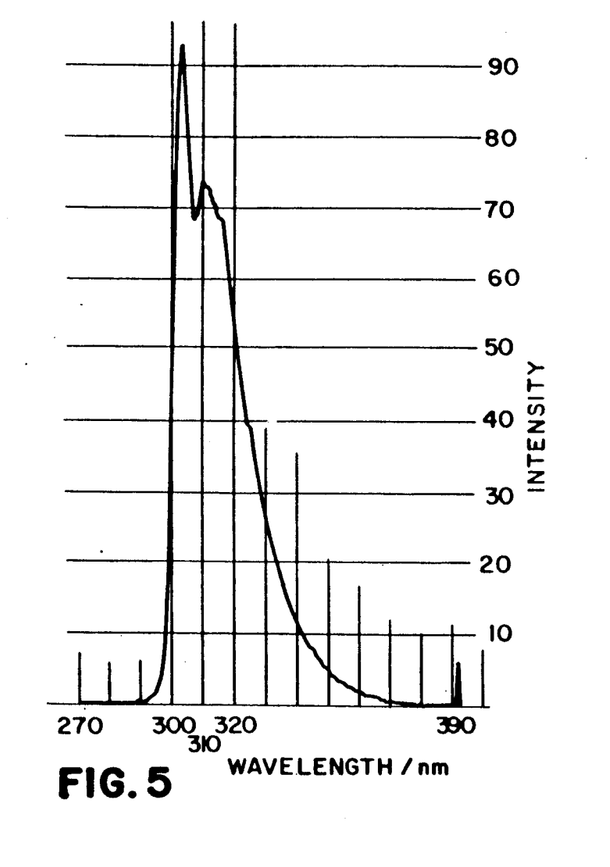
FIG. 5 is a fluorescence emission spectrum of fluorene.

The fluorescence emission spectrum for the dye 9,9-dipropylfluorene as illustrated in FIG. 1 was detected on a Perkin-Elmer MPF-44A, the slits were set at 2 nm and the excitation light was at 265 nm. The Fluorescence Quantum Efficiency (FQE) was about the same as that of fluorene - 55%; and the fluorescence emission peaks at 306 nm(intensity 86) and 316 nm(intensity 67) were also similar to those of fluorene [the fluorescence emission spectrum for fluorene as illustrated in FIG. 5 was also detected on a Perkin-Elmer MPF-44A, the slits were set at 2 nm and the excitation light was at 265 nm and the fluorescence emission peaks for fluorene are at 303 nm(intensity 93) and 311 nm(intensity 73)].

EXAMPLE 2

9,9,9',9'-Tetrapropyl-2,2'-bifluorene

The intermediate, 2-iodo-9,9-dipropylfluorene, was prepared as follows. A mixture of 25 g (0.1 mol) of 9,9-dipropylfluorene, 100 ml of acetic acid, 3.0 ml of sulfuric acid and 20 ml of water was heated to 75° C. Periodic acid dihydrate (4.56 g, 0.02 mol) and iodine (10.2 g 0.04 mol) were added to the heated mixture. The initial deep-purple color changed to a brown after one hour of heating and stirring at 75° C. After a second hour at that temperature, the mixture was diluted with an aqueous solution of sodium thiosulfate (7 g in 75 ml) added in portions. The mixture was washed into a separatory funnel with 100 ml of ethyl acetate, and the organic layer was washed repeatedly with water, 5% sodium hydroxide, and again with water. Removal of the ethyl acetate under reduced pressure gave a brown oil (29.5 g) which on crystallization from 45 ml of 2-propanol containing one ml of acetone gave 22.4 g of light yellow crystals, mp 79°–80° C. Recrystallization from the same solvents gave 18.4 g (49% of theory) of the product mp 80°–81°. NMR (CDCl$_3$): δ0.67 (s, 10H, —CH$_2$CH$_3$), 1.91 (m, 4H, —CH$_2$—), 7.23 (m, 3H, H-6, H-7 and H-8), 7.40–7.65 (m, 4H, remaining aromatics).

The dye, 9,9,9',9'-tetrapropyl-2,2'-bifluorene, was prepared from the intermediate as follows. To 250 ml of anhydrous DMF (from CaH$_2$) under a N$_2$ atmosphere was added 1.38 g (10.6 mMol) of yellow anhydrous nickel(II) chloride and 13.9 g (53 mMol) of triphenylphosphine (TPP). On heating at 50°–70° C. for two hours, the nickel salt dissolved and the solution took on the deep blue color of NiCl$_2$(TPP)$_2$. With the temperature at 50° C., zinc powder (0.877 g, 13.4 mMol) was added, and a color progression rapidly ensued (blue–green–yellow green–redbrown) After 15 minutes, the slurry of Ni(O) (TPP)$_3$ was treated with 5.0 g (13.3 mMol) of pulverized 2-iodo-9,9-dipropylfluorene. Stirring was continued for 20 hrs at 50° C. The mixture was cooled and was poured into 200 ml of 2% hydrochloric acid. Chloroform (50 ml) was added and the two-phase mixture was filtered through celite. The aqueous layer was washed twice with chloroform and the combined chloroform layer was washed five times with water, was dried (Na$_2$SO$_4$) and was concentrated to 21 g of an oil. Distillation of the oil at 0.01 torr allowed the recovery of 10.3 g of TPP, bp 80°–100° C. The viscous liquid remaining undistilled was dissolved in dichloromethane and was preabsorbed on 60 g of silica gel with complete removal of the solvent under reduced pressure. The preabsorbed sample was placed atop a column (90 cm diameter) of 140 g of silica gel packed with cyclohexane. Elution of 250 ml fractions gave the product in fractions 2 and 3 (1.15 g). Recrystallization from ethyl acetate gave 0.71 g (27% of the theory based on nickel chloride), mp 180°–181° C. Further recrystallization from the same solvent gave the analytical sample, mp 181°–183° C. NMR (CCl$_4$): δ0.75 (s, 20H, —CH$_2$CH$_3$), 2.07 (m, 8H, —CH$_2$—), 7.25 (m, 6H, aromatics on terminal rings), 7.43–7.78 (m, 8H, aromatic H's ortho to another ring).

Anal. Calcd for C$_{38}$H$_{42}$: C, 91.51; H, 8.49. Found: C, 91.41; H, 8.51.

Figure 2:
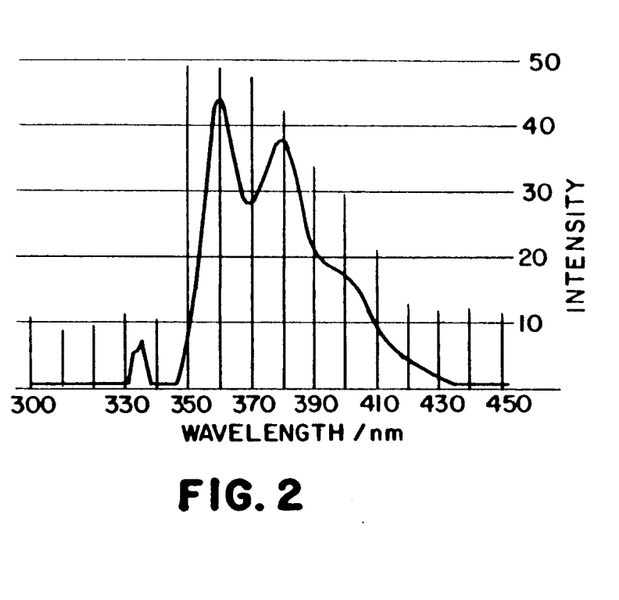
FIG. 2 is a fluorescence emission spectrum of 9,9,9',9'-tetrapropyl-2,2'-bifluorene.

This dye had two fluorescence peaks of almost equal intensity at 360 nm(intensity 33) and 378 nm(intensity 28) as illustrated in FIG. 2. It lased flashlamp pumped in ethanol/DMF, peaking at 382 nm; it displayed 45% greater useable lifetime than the commercial dye LD-390 which peaked at 386nm in the same system. The fluorescence emission spectrum of the dye 9,9,9',9'-tetrapropyl-2,2'-bifluorene was detected on a Perkin-Elmer MPF-44A, the slits were set at 2 nm and the excitation light was at 331 nm.

EXAMPLE 3

3-Phenyldibenzofuran

The dye, 3-phenyldibenzofuran, was prepared as follows. A mixture of 75 ml of water, 15 ml of 12 M hydrochloric acid (0.184 Mol), and 15.7 g of 3-aminodibenzofuran (0.0856 Mol) was stirred and cooled below 5°C. To it was added a solution of 6.2 g of sodium nitrite (0.0890 Mol) in 10 ml of water below 5° C. during about 30 min. Then 320 ml of chilled benzene was added, followed by a solution of 27 g of sodium acetate trihydrate (0.199 Mol) in 27 ml of water dropwise at 5°–10° C. The mixture was allowed to warm to 20° C. overnight, stirred, and heated at 50° C. for 5 hours in a water bath. The organic layer was washed with 200 ml of 6 M sodium hydroxide, 2×200 ml of warm 10% 2-propanol, 200 ml of 1 M hydrochloric acid containing 10% 2-propanol, then stirred and warmed with 10 g of magnesium sulfate and 2 g of activated carbon for 3 days. The solution was filtered, then the solvent was removed under vacuum, leaving 19 g of gummy residue, which was sublimed at 200° C. and 0.45 torr to give 6.14 g of a solid, mp 65°–115° C. This solid was recrystallized from 2-propanol to give 5.6 g of a tan product, mp 132°14 132.5° C. (lit. mp 132.5° C.). Further purification was accomplished by continuous extraction of the tan solid from 20 g of Brockmann activity I alumina in an Ace/Kauffman column with Freon TF, to yield 5.00 g of white product, mp 132°–133.5° C.

Figure 3:
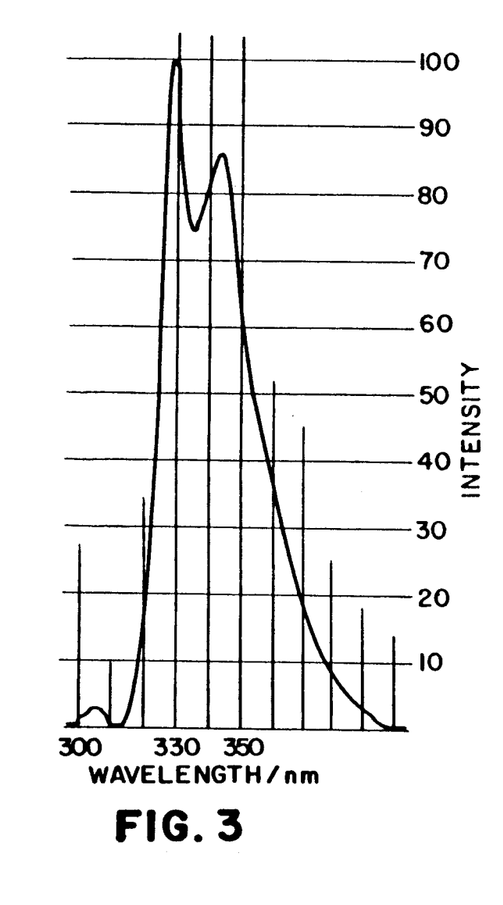
FIG. 3 is a fluorescence emission spectrum of 3-phenyldibenzofuran.

In all cases the solubility (See Table I) was much greater than that of p-terphenyl, which enables much wider applications in various solvents, such as in the lower alcohols. This dye had fluorescence peaks at 324 nm(intensity 90) and 338 nm(intensity 76) and a reported fluorescence quantum yield of 100% in cyclohexane as illustrated in FIG. 3. It was also found that the FQE was the same in methanol as in cyclohexane. The fluorescence emission spectrum for the dye 3-phenyldibenzofuran as illustrated in FIG. 3 was detected on a Perkin-Elmer MPF-44A, the slits were set at 2 nm and the excitation light was at 301 nm.

EXAMPLE 4

3,3'-Bi(dibenzofuran)

Figure 4:
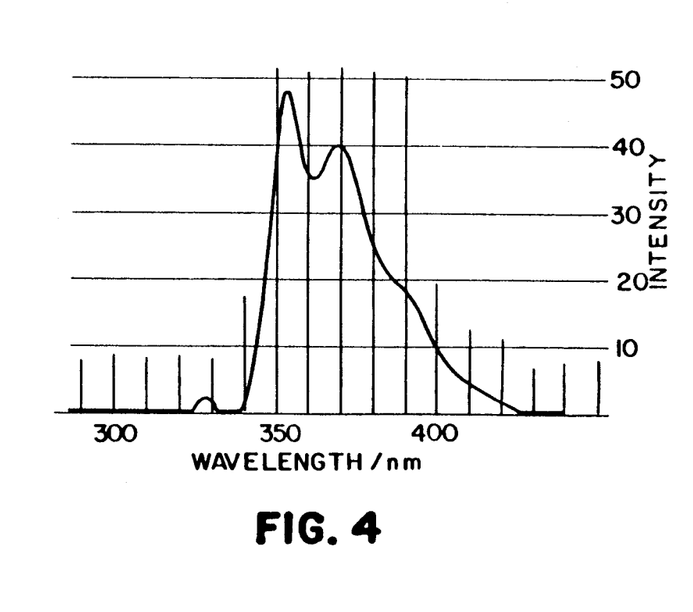
FIG. 4 is a fluorescence emission spectrum of 3,3'-bi(dibenzofuran)

The dye, 3,3'-bi(dibenzofuran), was prepared in accordance with the process disclosed in H. O. Wirth, G. Waese and W. Kern: Synthese Und Eigenschaften Von: Oxydo-p-oligophenylenen. *Makromol. Chem.* 86: 139(1965) which is incorporated herein in its entirety by reference, and was purified by extraction from Brockmann Activity I alumina with chloroform in an Ace-Kauffman column to give a white solid, mp 249.5°–250.5° C. (lit.mp 252.5° C.). This dye had two fluorescence peaks of almost equal intensity at 353 nm(intensity 47) and 369 nm(intensity 30) in cyclohexane as illustrated in FIG. 4. Its fluorescence emission spectrum was almost superimposable on that of the dye discussed in Example 2. Its solubility was greater than that of 2,2'-bifluorene, as shown in Table I. The fluorescence emission spectrum for the dye 3,3'-bi(dibenzofuran) as illustrated in FIG. 4 was detected on a Perkin-Elmer MPF-44A, the slits were set at 2 nm and the excitation light was at 323 nm.

EXAMPLE 5

9,9'-Diethyl-2,2'-Bicarbazole

The intermediate, 2-bromo-9-ethylcarbazole, was prepared as follows. A mixture of 8.5 g (35 mMol) of 2-bromocarbazole, 2.1 g (53 mMol) of powdered sodium hydroxide and 17 ml of 2-butanone was heated slowly to reflux. Iodoethane (6 ml, 75 mMol) was added dropwise for 30 min. to the refluxing solution, and refluxing was continued for 12 hrs. An additional 1.05 g of sodium hydroxide and 3.0 ml of iodoethane were added as before and the reflux was continued for 18 hours. Removal of the solvent under reduced pressure gave a mixture which was partitioned between water and ethyl acetate. The organic layer was washed with water, dried and was concentrated to give the crude product. Crystallization from 10 ml of methanol gave 6.66 g (70% of theory) of product, mp 93°–4° C. NMR (CDCl$_3$) δ1.31 (t, 3H, CH$_3$), 4.11 (q, 2H, NCH$_2$) 6.98–7.43 (m, 5H, aromatic), 7.75–8.05 (m, 2H, H-4 and H-5).

The dye, 9,9'-diethyl-2,2'-bicarbazole, was prepared from the above intermediate as follows. To a mixture of 1.10 g (4 mMol) of 2-bromo-9-ethylcarbazole and 0.096 g of cut magnesium ribbon in 4 ml of refluxing ether was added 50 microliters of 1,2-dibromoethane. Refluxing was continued for 18 hrs. The solution was cooled and 386 microliters (0.455 g) of cis-1,4-dichloro-2-butene was added. As the solution was returned to reflux, a precipate appeared. After three hours the mixture was filtered. The solid was recrystallized from 2-methoxyethanol with a hot filtration to give 0.124 g (12% of theory) of product, mp 239°–40° C. This compound exhibited a brighter violet fluorescence in alcohols than the compounds of Examples 2 and 4.

The present invention may, of course, be carried out in other specific ways than those herein set forth without departing from the spirit and essential characteristics of the invention. The present embodiments are, therefore, to be considered in all respects as illustrative and not restrictive and any changes coming within the meaning and equivalency range of the appended claims are to be embraced therein.

Having described in detail the preferred embodiments of our invention, what we desire to claim and protect by Letters Patent is:

1. An organic laser dye solution being capable of generating coherent laser radiation in a wave length range from about 300 nm up to about 420 nm when excited by a pumping light source, said organic laser dye solution comprising:

an oligophenylene having at least one biphenyl moiety bridged between adjacent ortho positions via a substituent selected from the group consisting of CHR', NH and NR' wherein R' is alkyl, aryl, substituted alkyl and aryl, halogen, alkoxy, alkoxyalkyl, aryloxy, dialkylamino and dialkylaminoalkyl and salts thereof, and alkylcarboxylic acids, esters and salts thereof; and solvent which does not substantially interfere with the emission, said oligophenylene being present in said solvent in a concentration which enables said organic laser dye solution to generate the coherent laser radiation in the wave length range when excited by the pumping light source.

2. An organic laser dye solution of claim 1, said oligophenylene having from 1 to about 4 biphenyl moieties.

3. An organic laser dye solution of claim 1, said solvent being a polar solvent.

4. An organic laser dye solution of claim 3, said polar solvent being selected from the group consisting of an alcohol solvent and an aqueous mixture solvent.

5. An organic laser dye solution of claim 1 wherein each of the phenyl groups of the biphenyl moiety are free of vinylene groups bonded directly thereto.

6. An organic laser dye solution being capable of generating coherent laser radiation when excited by a pumping light source, said organic laser dye solution comprising:

an organic o,o'-bridged oligophenylene laser dye of the general formula:

wherein X represents CHR', NH and NR';
R' is alkyl, aryl, substituted alkyl and aryl, halogen, alkoxy, alkoxyalkyl, aryloxy, dialkylamino and dialkylaminoalkyl and salts thereof, and alkylcarboxylic acids, esters and salts thereof;
R represents H, alkyl, aryl, substituted alkyl and aryl, halogen, alkoxy, alkoxyalkyl, aryloxy, dialkylamino and dialkylaminoalkyl and salts thereof, sulfonic, alkylsulfonic, alkylphosphonic and alkylcarboxylic acids, esters and salts thereof, fluorinated alkyl and aryl, NH₂, and NHR' and NR'₂ and salts thereof; and
n represents 1 to about 4; and
a solvent which does not interfere with the emission, said organic o,o'-bridged oligophenylene laser dye being present in said solvent in a concentration which enables said organic laser dye solution to generate the coherent laser radiation when excited by the pumping light source.

7. An organic laser dye solution of claim 6 wherein said dye is 9,9'-diethyl-2,2'-bicarbazole.

8. An organic laser dye solution being capable of generating coherent laser radiation when excited by a pumping light source, said organic laser dye solution comprising:

an oligophenylene having at least 1 biphenyl moiety bridged between adjacent ortho positions via a carbon atom being free of benzylic hydrogens and a solvent which does not interfere with the emission, said oligophenylene having improved stability and solubility in said solvent due to the absence of benzylic hydrogens and being present in said solvent in a concentration which enables said organic laser dye solution to generate the coherent laser radiation when excited by the pumping light source.

9. An organic laser dye solution of claim 8 wherein each of the phenyl groups of the biphenyl moiety are free of vinylene groups bonded directed thereto.

10. An organic laser dye solution of claim 8 wherein said oligophenylene is a continuous oligophenylene chain containing from between about 3 to about 8 phenyl groups.

11. A new composition of matter having the following structure:

12. A new composition of matter having the following structure:

13. A new composition of matter having the following structure:

14. An organic laser dye solution being capable of generating coherent laser radiation when excited by a pumping light source, said organic laser dye solution comprising:

an organic o,o'-bridged oligophenylene laser dye having the following formula:

said o,o'-bridged oligophenylene laser dye being characterized as 3-phenyldibenzofuran; and
a solvent which does not interfere with the emission, said 3-phenyldibenzofuran being present in said solvent in a concentration which enables said organic laser dye solution to generate the coherent laser radiation when excited by the pumping light source.

15. An organic laser dye solution capable of generating coherent laser radiation in a wave length range from about 300 nm up to about 420 nm when excited by a pumping light source, said organic laser dye solution comprising:
an oligophenylene having at least one biphenyl moiety bridged between adjacent ortho positions via an CR'$_2$ substituent wherein R' is alkyl, aryl, substituted alkyl and aryl, halogen, alkoxy, alkoxyalkyl, aryloxy, alkylsulfonic acids, esters and salts thereof, dialkylamino and dialkylaminoalkyl and salts thereof, and alkylcarboxylic acids, esters and salts thereof; and
a solvent which does not substantially interfere with the emission, said oligophenylene being present in said solvent in a concentration which enables said organic laser dye solution to generate the coherent laser radiation in the wave length range when excited by the pumping light source.

16. An organic laser dye solution of claim 15, said oligophenylene having from 1 to about 4 biphenyl moieties.

17. An organic laser dye solution of claim 15, said solvent being a polar solvent.

18. An organic laser dye solution of claim 17, said polar solvent being selected from the group consisting of an alcohol solvent and an aqueous mixture solvent.

19. An organic laser dye solution of claim 15 wherein each of the phenyl groups of the biphenyl moiety are free of vinylene groups bonded directed thereto.

20. An organic laser dye solution capable of generating coherent laser radiation when excited by a pumping light source, said organic laser dye solution comprising:
an organic o,o'-bridged oligophenylene laser dye of the general formula:

wherein X represents CR'$_2$;
R' is alkyl, aryl, substituted alkyl and aryl, halogen, alkoxy, alkoxyalkyl, aryloxy, alkylsulfonic acids, esters and salts thereof, dialkylamino and dialkylaminoalkyl and salts thereof, and alkylcarboxylic acids, esters and salts thereof;
R represents H, alkyl, aryl, substituted alkyl and aryl, halogen, alkoxy, alkoxyalkyl, aryloxy, dialkylamino and dialkylaminoalkyl and salts thereof, sulphonic, alkylsulphonic, alkylphosphonic and alkylcarboxylic acids, esters and salts thereof, fluorinated alkyl and aryl, NH$_2$, and NHR' and NR'$_2$ and salts thereof;
n represent 1 to about 4; and
a solvent which does not interfere with the emission, said organic o,o'-bridged oligophenylene laser dye being present in said solvent in a concentration which enables said organic laser dye solution to generate the coherent laser radiation when excited by the pumping light source.

21. An organic laser dye solution of claim 20 wherein said dye is 9,9-dipropylfluorene.

22. An organic laser dye solution of claim 20 wherein said dye is 9,9,9',9'-tetrapropyl-2,2'-bifluorene.

* * * * *